US010137102B2

(12) United States Patent
Pirttilä et al.

(10) Patent No.: US 10,137,102 B2
(45) Date of Patent: Nov. 27, 2018

(54) OLIGOMERIC FORMS OF 3-HYDROXYBUTYRATE

(71) Applicant: Oulun Yliopisto, Oulun Yliopisto (FI)

(72) Inventors: Anna Maria Pirttilä, Oulu (FI); Janne Koskimäki, Oulu (FI); Sampo Mattila, Oulu (FI); Marena Kajula, Oulu (FI); Juho Hokkanen, Oulu (FI); Bruce Campbell, Oulu (FI)

( * ) Notice: Subject to any disclaimer, the term of this patent is extended or adjusted under 35 U.S.C. 154(b) by 0 days.

(21) Appl. No.: 15/327,395

(22) PCT Filed: Jul. 21, 2015

(86) PCT No.: PCT/FI2015/050509
§ 371 (c)(1),
(2) Date: Jan. 19, 2017

(87) PCT Pub. No.: WO2016/012657
PCT Pub. Date: Jan. 28, 2016

(65) Prior Publication Data
US 2017/0196826 A1    Jul. 13, 2017

(30) Foreign Application Priority Data

Jul. 21, 2014  (FI) ..................................... 20145687

(51) Int. Cl.
*A61K 31/22* (2006.01)
*A61K 9/00* (2006.01)
(52) U.S. Cl.
CPC ............ *A61K 31/22* (2013.01); *A61K 9/0048* (2013.01)
(58) Field of Classification Search
CPC ............................... A61K 31/22; A61K 9/0048
See application file for complete search history.

(56) References Cited

U.S. PATENT DOCUMENTS

| 5,116,868 A | 5/1992 | Chen et al. |
|---|---|---|
| 7,825,134 B2 | 11/2010 | Matier et al. |
| 8,541,468 B2 | 9/2013 | Umeda et al. |
| 2002/0013339 A1 | 1/2002 | Martin et al. |
| 2009/0253781 A1 | 10/2009 | Veech |

FOREIGN PATENT DOCUMENTS

| EP | 0780123 A1 | 6/1997 |
|---|---|---|
| JP | 2003313123 A | 11/2003 |
| JP | 200565652 A | 3/2005 |
| WO | WO9841200 A1 | 9/1998 |
| WO | WO0004895 A2 | 2/2000 |
| WO | WO2006020137 A2 | 2/2006 |
| WO | WO2006020179 A2 | 2/2006 |
| WO | WO2006110034 A1 | 9/2008 |
| WO | WO2009089144 A1 | 7/2009 |
| WO | WO2013150153 A1 | 10/2013 |

OTHER PUBLICATIONS

Adijanto Jeffrey at at: The Retinal Pigment Epithelium Utilizes Fatty Acids for Ketogenesis. The Journal of Biological Chemistry, vol. 289, No. 30, Jul. 25, 2014, pp. 20570-20582.
Gambhir Deeksha et al: Modulating inflammation in retina through targeting of GPR109A: Novel implication for therapeutic management of diabetic retinopathy. Investigative Ophthalmology & Visual Science, vol. 54, Jun. 2013, p. 1772.
Jarrett Stuart et al: Consequences of oxidative stress in age-related macular degeneration. Molecular Aspects of Medicine, vol. 33, Issue 4, Aug. 2012, pp. 339-417.
Kauppinen Anu et al: Oxidative stress activates NLRP3 inflammasomes in ARPE-19 cells—Implications for age-related macular degeneration (AMD). Immunology Letters, vol. 147, Issues 1-2, Sep.-Oct. 2012, pp. 29-33.
Martin Pamela et al: Expression of the Niacin Receptor GPR109A in Retina: More than Meets the Eye? Journal of Clinical and Experimental Pharmacology, S3, 2013.
Nakamura Shigeru et al: Protective Effect of D-β-Hydroxybutyrate on Corneal Epithelia in Dry Eye Conditions through Suppression of Apoptosis. Investigative Ophthalmology & Visual Science, vol. 44, No. 11, Nov. 2003, pp. 4682-4688.
Thaler Sebastian et al: Neuroprotection by acetoacetate and β-hydroxybutyrate against NMDA-induced RGC damage in rat—possible involvement of kynurenic acid. Graefes Arch Clin Exp Ophthalmol, No. 248, 2010, pp. 1729-1735.
Uchino Yuichi et al: Oxidative Stress Induced Inflammation Initiates Functional Decline of Tear Production. Published Oct. 5 2012, https://doi.org/10.1371/journal.pone.0045805.
Wakamatsu Tais et al: Evaluation of Lipid Oxidative Stress Status in Sjögren Syndrome Patients. Investigative Ophthalmology & Visual Science, Jan. 2013, vol. 54, No. 1, pp. 201-210.
Winkler Barry et al: Oxidative damage and age-related macular degeneration. National Institutes of Health, Mol Vis., Author manuscript, Available in PMC, Jan. 17 2007.
Athlan Audrey et al: Abiotic Aging of Water-Soluble 3-Hydroxybutyric Acid Oligomers as Monitored by Capillary Zone Electrophoresis. Journal of Environmental Polymer Degradation, vol. 5, No. 4, 1997, pp. 243-247.
Berge Stephen M. et al: Pharmaceutical salts. Journal of Pharmaceutical Sciences, Jan. 1977, vol. 68, No. 1, pp. 1-19.
Haces Maria L. et al: Antioxidant capacity contributes to protection of ketone bodies against oxidative damage induced during hypoglycemic conditions Experimental Neurology, vol. 211, 2008, pp. 85-96.
Hohtola Anja: Seasonal changes in explant viability and contamination of tissue cultures from mature Scots pine. Plant Cell, Tissue and Organ Culture, vol. 15, 1988, pp. 211-222.
Kehrer James P.: The Haber-Weiss reaction and mechanisms of toxicity. Toxicology, vol. 149, 2000, pp. 43-50.

(Continued)

*Primary Examiner* — Sudhakar Katakam
(74) *Attorney, Agent, or Firm* — Seppo Laine Oy

(57) ABSTRACT

The present invention relates to medicaments based on oligomeric forms of 3-hydroxybutyrate, particularly 3-hydroxybutyrate methyl ester dimer (1) and trimer (2), especially for use in treating, preventing and/or inhibiting development of a disorder or condition related to oxidative stress. The present invention relates also to the use of these molecules as antioxidants, and to a method for increasing proliferation and viability of plant cells in the aid of molecules 1 and 2.

12 Claims, 2 Drawing Sheets

(56) References Cited

OTHER PUBLICATIONS

Moore Jeffrey et al: Novel Fluorometric Assay for Hydroxyl Radical Scavenging Capacity (HOSC) Estimation. Journal of Agricultural and Food Chemistry, vol. 54, 2006, pp. 617-626.

Ou Boxin et al: Development and Validation of an Improved Oxygen Radical Absorbance Capacity Assay Using Fluorescein as the Fluorescent Probe. Journal of Agricultural and Food Chemistry, 2001, vol. 49, pp. 4619-4626.

Pirttila Anna Maria et al: Detection of Intracellular Bacteria in the Buds of Scotch Pine (*Pinus sylvestris* L.) by In Situ Hybridization. Applied and Environmental Microbiology, vol. 66, No. 7, Jul. 2000, pp. 3073-3077.

Pirttilä Anna Maria et al: Role of origin and endophyte infection in browning of bud-derived tissue cultures of Scots pine. Plant Cell Tiss Organ Cult, 2008, vol. 95, pp. 47-55.

Shimazu Tadahiro et al: Suppression of Oxidative Stress by β-Hydroxybutyrate, an Endogenous HistoneDeacetylase Inhibitor. Science, vol. 339, 2013, pp. 211-214.

Vasala Antti et al: A new wireless system for decentralised measurement of physiological parameters from shake flasks. Microbial Cell Factories, Feb. 24, 2008, pp. 1-6.

Li Jun et al: Conformational Analysis of Oligomers of (R)-3-Hydroxybutanoic Acid in Solutions by HNMR Spectroscopy. Bulletin of the Chemical Society of Japan, vol. 71, No. 7, Jan. 1, 1998, pp. 1683-1689.

Tanaka Yoshimasa et al: Purification and Properties of d(−)-3-Hydroxybutyrate-Dimer Hydrolase from Zoogloea ramigera I-16-M. European Journal of Biochemistry, vol. 118, No. 1, Jan. 8, 1981, pp. 177-182.

Tasaki O et al: The dimer and trimer of 3-hydroxybutyrate oligomers as a precursor of ketone bodies for nutritional care. JPEN, vol. 23, No. 6, Jan. 1, 1999, pp. 321-325.

Zarnowski et al: A ketogenic diet may offer neuroprotection in glaucoma and mitochondrial diseases of the optic nerve. Medical Hypothesis, Discovery and Innovation in Ophthalmology, Jan. 1, 2012, p. 45.

OLIGOMERIC FORMS OF 3-HYDROXYBUTYRATE

TECHNICAL FIELD

The present invention relates to oligomeric forms of 3-hydroxybutyrate, particularly 3-hydroxybutyrate methyl ester dimer and trimer and their use as medicaments and antioxidants. The present invention also relates to a method of increasing proliferation and viability of cells, particularly plant cells, by growing them in the presence of molecules of the present invention.

BACKGROUND ART

Oxidative stress reflects an imbalance between the systemic manifestation of reactive oxygen species and a biological system's ability to readily detoxify the reactive intermediates or to repair the resulting damage. Disturbances in the normal redox state of cells can cause toxic effects through the production of peroxides and free radicals that damage all components of the cell.

In humans, oxidative stress is thought to be involved in the development of various disorders and diseases, such as cancer, Parkinson's disease, Alzheimer's disease, atherosclerosis, heart failure, myocardial infarction, fragile X syndrome, Sickle Cell Disease, lichen planus, vitiligo, autism, and chronic fatigue syndrome, certain cardiovascular diseases and ischemia. Oxidative stress also contributes to tissue injury following irradiation and hyperoxia, as well as in diabetes. Oxidative stress is also thought to contribute to the aging process and age related cancer. The reactive species produced in oxidative stress can cause direct damage to the DNA and are therefore mutagenic, and it may also suppress apoptosis and promote proliferation, invasiveness and metastasis. Infection by *Helicobacter pylori* which increases the production of reactive oxygen and nitrogen species in human stomach is also thought to be important in the development of gastric cancer.

Chemically, oxidative stress is associated with increased production of oxidizing species or a significant decrease in the effectiveness of antioxidant defenses, such as glutathione.

Production of reactive oxygen species (ROS), such as free radicals and peroxides, is a particularly destructive aspect of oxidative stress.

An antioxidant is a molecule that inhibits the oxidation of other molecules. Antioxidants are often reducing agents, such as thiols, ascorbic acid, or polyphenols.

Also some keto compounds, such as 3-hydroxy butyrate have been used. Pharmaceutical compositions of 3-hydroxy butyrate and oligomers thereof suggested for treatment of neurodegenerative disorders, such as Alzheimer's disease, are disclosed in WO 2006020179, US 2009253781 and WO 0004895. These documents also disclose similar compositions for neutriceutical use.

The use of antioxidants in pharmacology is intensively studied, particularly as treatments for stroke and neurodegenerative diseases. According to National Institute of Health report, scientific studies involving more than 100,000 people combined have tested whether antioxidant supplements such as vitamins C and E, selenium, and carotenoids can help prevent chronic diseases. In most instances, antioxidants did not reduce the risks of developing these diseases.

Accordingly, there is still need for developing further antioxidants.

SUMMARY OF INVENTION

Technical Problem

It is an aim of the present invention to provide pharmaceutically active compounds for use as antioxidants and for treating, preventing or inhibiting development of a disease, disorder or condition related to oxidative stress.

It is another aim to provide pharmaceutically active compounds for treating, preventing or inhibiting development of ophthalmic degeneration, such as ocular or retinar degeneration. The oculus and the retina are particularly subjected to UV induced formation of oxygen radicals and the subsequent degeneration caused thereby.

Solution to Problem

In the present invention, it has been observed that molecules of general formula I,

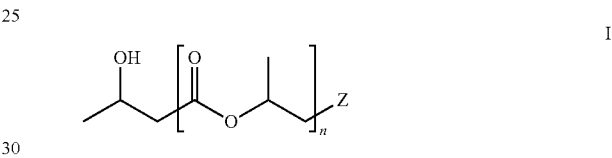

wherein
Z is a carboxylic acid, or a pharmaceutically acceptable salt, or an ester thereof, and
n is an integer of 1 or 2,
increase viability of prokaryotic and eukaryotic cells by alleviating oxidative stress.

In particular, the novel molecules of formula I are useful as medicaments in therapy when said molecules are in uncleaved form in vivo.

Based on this finding, the present invention provides for novel pharmaceutical uses of the molecules according to general formula I, for example as protective agents against oxidative stress of cells and—more generally—as antioxidants and food additives and as components of microorganisms' growth media.

The invention also provides for pharmaceutical compositions and for the use of the molecules of general formula I for increasing of proliferation and viability of cells, such as cells of plants and animals, including culturing the cells.

The following presents a simplified summary in order to provide a basic understanding of some aspects of various embodiments of the invention. The summary is not an extensive overview of the invention. It is neither intended to identify key or critical elements of the invention nor to delineate the scope of the invention. The following summary merely presents some concepts of the invention in a simplified form as a prelude to a more detailed description of exemplifying embodiments of the invention.

According to one aspect the present invention concern molecules of general formula I, wherein n is 1 or 2 for use as a medicament.

According to another aspect the present invention concerns a molecule of general formula I wherein n is 1 or 2 for use in treating, preventing and/or inhibiting development of a disorder or condition related to oxidative stress.

According to another aspect the present invention concerns pharmaceutical composition comprising a molecule of general formula I, wherein n is 1 or 2 and one or more excipients and preferably also a pharmaceutically suitable carrier.

According to another aspect the present invention concerns use of a molecule of general formula I wherein n is 1 or 2 as an antioxidant.

According to another aspect the present invention concerns use of a molecule of general formula I wherein n is 1 or 2 as a food additive.

According to another aspect the present invention concerns the use of a molecule of general formula I wherein n is 1 or 2 as a protecting agent against oxidative stress of cells.

According to another aspect the present invention concerns a method for increasing of proliferation and viability of cells, such as animal or in particular plant cells, including culturing the cells in the presence of one or more molecules of general formula I, wherein n is 1 or 2.

In all the above aspects, the molecules of general formula I are, in vivo, present in uncleaved form.

A number of exemplifying and non-limiting embodiments of the invention are described in accompanied dependent claims.

Various exemplifying and non-limiting embodiments of the invention both as to constructions and to methods of operation, together with additional objects and advantages thereof, will be best understood from the following description of specific exemplifying embodiments.

The verbs "to comprise" and "to include" are used in this document as open limitations that neither exclude nor require the existence of also un-recited features. The features recited in depending claims are mutually freely combinable unless otherwise explicitly stated. Furthermore, it is to be understood that the use of "a" or "an", i.e. a singular form, throughout this document does not exclude a plurality.

In the present context, when discussing the present compounds, enantiomers as well as racemic forms are included.

Advantageous Effects of Invention

Based on hydroxyl radical scavenging assays the dimeric (general formula I, n=1) and trimeric (general formula I, n=2) molecules show more than tenfold higher antioxidant capacity against hydroxyl radicals over the known antioxidants than the monomeric compound 3-hydroxybutyric acid or ascorbic acid and thus protect ROS challenged cells effectively from oxidative damage in low concentrations. Excellent antioxidant activity will be reached, for example in ophthalmic therapy.

Further, the present molecules are water-soluble or water-dispersible which allows for facile formulation and administration of them.

It appears that the 3-hydroxybutyrate oligomers of the known pharmaceutical compositions, when administered orally, will decompose to the monomeric forms metabolically thus significantly reducing their activity.

By contrast, when the present oligomers are formulated for administration such as to prevent decomposition, in particular in the gastrointestnal tract. Therefore the oligomers will reach their therapeutic target site in vivo in an uncleaved, non-decomposed form. Therefore, no loss of activity of the administered compound will occur.

DESCRIPTION OF EMBODIMENTS

Figure 1:
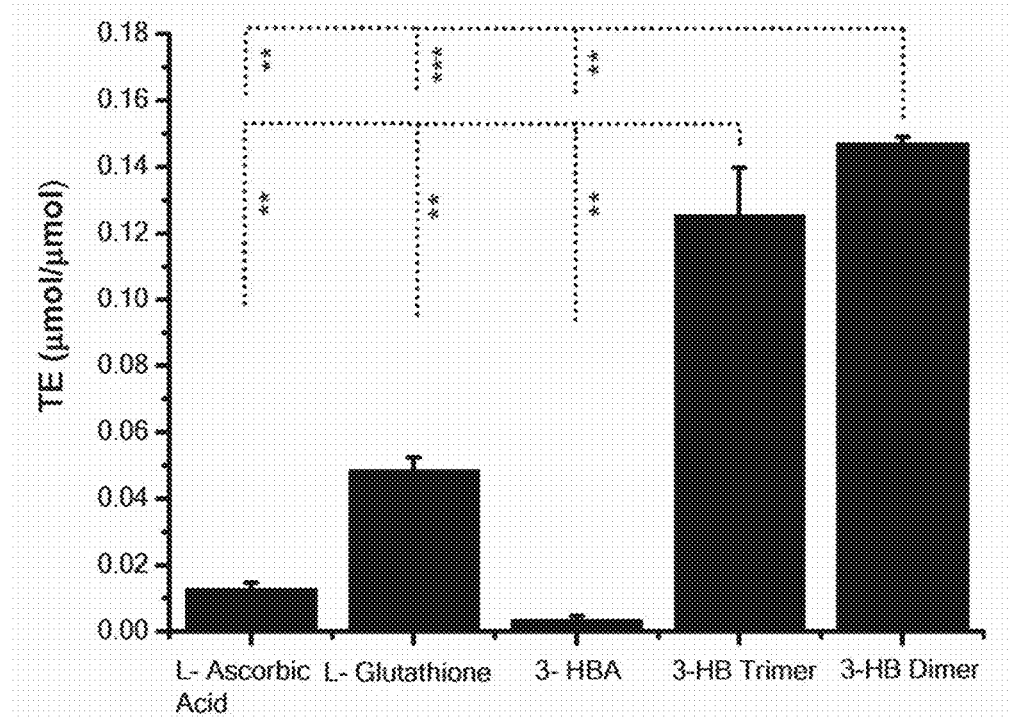
FIG. 1 is a bar chart showing hydroxyl radical scavenging activity (from left to right) of ascorbic acid, glutathione, 3-hydroxybutyric acid (3-HBA), 3-HB dimer (compound 1) 3-HB trimer (compound 2) in fluorometric .OH scavenging capacity (HOSC) assay.

As disclosed in the present invention, molecules of general formula I

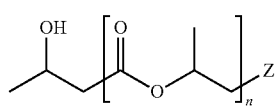

wherein
Z is a carboxylic acid, a pharmaceutically acceptable salt or an ester thereof, and
n is an integer 1 or 2, have been found to exhibit valuable pharmacological activity.

Particularly those wherein Z is COOMe, and n is 1 or 2 increase viability of prokaryotic and eukaryotic cells by alleviating oxidative stress significantly better than 3-hydroxybutyric acid known in the art.

According to one embodiment the present invention concerns molecules of general formula I, wherein n is 1 or 2, and wherein Z is selected from the group of carboxylic acids (Z=COOH), pharmaceutically acceptable salts and esters (COOR) thereof, for use as a medicament.

The term "pharmaceutically acceptable salt" is defined in the review article of Berge et al. [J. Pharm Sci, 66, 1977, 1].

Exemplary pharmaceutically salts of molecules of general formula I wherein Z is COO⁻ are sodium, potassium, lithium, magnesium, calcium, and ammonium salts.

According to one embodiment the molecules of general formula I used as a medicament are esters, i.e. wherein Z is COOR. Exemplary esters are alkyl and aryl esters. Alkyl esters, in particular lower alkyl esters, are preferable. "Lower alkyl esters" are esters in which the alkyl of the alcohol residue has 1 to 6, in particular 1 to 4 carbon atoms. Exemplary alkyl groups are methyl, ethyl, n-propyl, i-propyl, n-butyl, sec-butyl and tert-butyl. A particular alkyl group is methyl. The alkyl group may include also heteroatoms, such as one or more of the following: halogen, oxygen, sulfur and mixtures thereof.

Particular molecules of general formula I of the present invention for use as a medicament are the following:

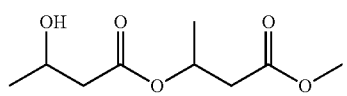

1

-continued

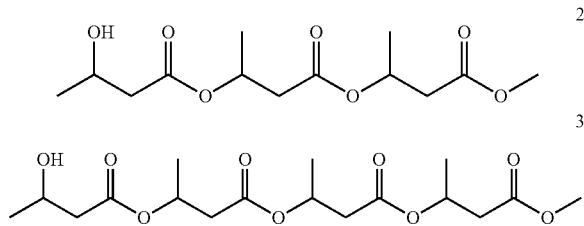

Particularly preferable molecules for use as a medicament are the dimer (formula 1) and the trimer (formula 2). These molecules of general formula I are water soluble and they can enter cells by simple diffusion or they can be carried by transporters.

According to another embodiment the molecules of general formula I used as a medicament carboxylic acids, i.e. wherein Z is COOH and their pharmaceutically acceptable salts. Exemplary pharmaceutically salts of molecules of General formula I wherein Z is COO— are sodium, potassium, lithium, magnesium, calcium, and ammonium salts.

Particular molecules of general formula I of the present invention for use as a medicament are the following:

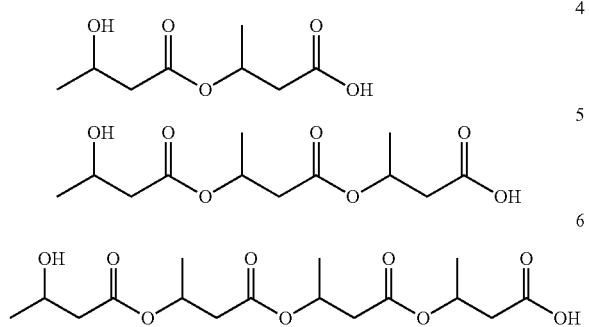

It should be noted that monomeric 3-hydroxy fatty acid and its derivatives are known in the art as active components of pharmaceutical composition for improving of learning and/or memory of subjects. Thus, WO2008110034 teaches that use of the compounds in the manufacture of medicaments for improving of learning and/or memory of subjects. WO2008110034 is silent about the use of the compounds for the present uses. Nutritional and therapeutic uses of 3-hydroxyalkanoate oligomers are disclosed in US 20020013339. Particularly preferable molecules for use as a medicament are the dimer (4) and the trimer (5). These molecules of general formula I are water soluble and they can enter cells by simple diffusion or they can be carried by transporters. The structures of molecules 4, 5 and 6 shown above are drawn as free acids. It is however obvious that the present invention concerns also the corresponding carboxylate ions and pharmaceutically acceptable salts.

According to another embodiment the present invention concerns molecules of general formula I wherein n is an integer of 1 or 2, for use in treating, preventing and/or inhibiting development of a disease, disorder or condition related to oxidative stress. Exemplary diseases are cancer, Parkinson's disease, Alzheimer's disease, atherosclerosis, heart failure, myocardial infarction, fragile X syndrome, Sickle Cell Disease, lichen planus, vitiligo, autism, chronic fatigue syndrome, and infection by *Helicobacter pylori*. Particular diseases, disorders or conditions are neurodegenerative disorders including but not limited to Lou Gehrig's disease, Parkinson's disease, Alzheimer's disease, Huntington's disease, and Multiple sclerosis.

Particular molecules of general formula I of the present invention for use in treating, preventing and/or inhibiting disease, disorder or condition related to oxidative stress are the following (i.e. molecules of general formula I, wherein Z is methyl ester):

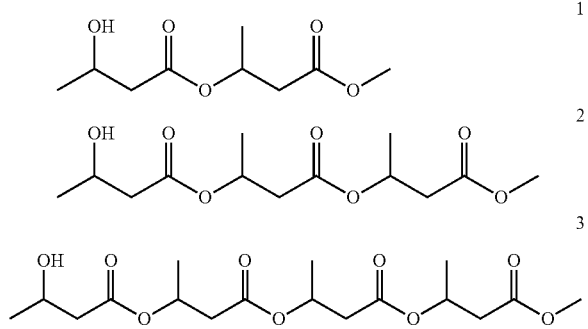

Particularly preferable molecules are the dimer (1) and the trimer (2).

According to one embodiment the present invention concerns molecules of general formula I wherein the n is an integer 1 to 10, in particular 1 to 5, for example 1 to 4, advantageously 1 to 3, preferably 1 or 2, for use in treating, preventing and/or inhibiting development of neurodegenerative disorders of the pancreas as well as ophthalmic disorders, in particular disorders selected from the group of retinal neurodegenerative disorder, including but not limited to retinitis pigmentosa, age-related macular degeneration, glaucoma, diabetic retinopathy.

Particular molecules of general formula I for use in treating, preventing and/or inhibiting development of the neurodegenerative disorder are the following (i.e. molecules of general formula I, wherein Z is methyl ester):

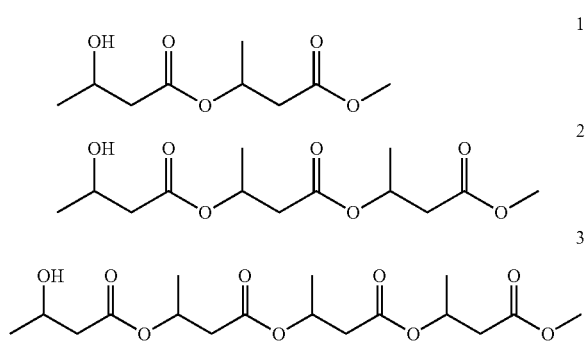

Particularly preferred molecules are the dimer (1) and the trimer (2).

According to another embodiment the molecule of general formula I,

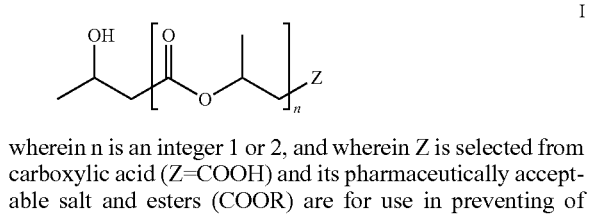

wherein n is an integer 1 or 2, and wherein Z is selected from carboxylic acid (Z=COOH) and its pharmaceutically acceptable salt and esters (COOR) are for use in preventing of apoptosis, wherein the apoptosis is in particular related to diabetes type I, diabetes type II, wet age-related macular degeneration AMD (in combinations with known pharmaceutical, such as Lucentis), dry AMD, non-arteritic anterior ischemic optic neuropahthy (NAION), diabetic retinopathy, retinitis pigmentosa, glaucoma, acute labyrinthitis, herpes simplex infection leading corneal blindness, spinal cord injuries, traumatic brain injury, sepsis (survival of T-cells/effector cells), fatty liver (non-alcoholic steatohepatitis), Parkinson's disease, Alzheimers disease, Huntington disease, stroke, myocardial infarct and ischemia.

Compositions comprising molecule of general formula I wherein n is an integer 1 or 2, according to various embodiments of this invention may be formulated, for instance, as pharmaceutical compositions, food additives, food products, natural products, or heath products.

Accordingly, the present invention concerns also use of molecules of general formula I

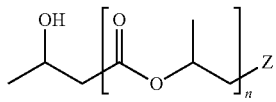

wherein n is an integer from 1 or 2, and wherein Z is selected from carboxylic acid (Z=COOH), and its pharmaceutically acceptable salt and an ester (COOR) as a food additive. According to a particular embodiment, the molecules of general formula I are selected from the following:

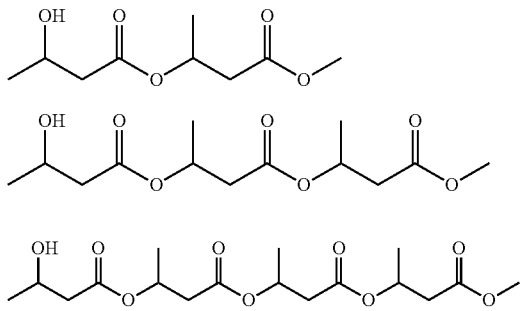

Particularly preferred molecules are the dimer (1) and the trimer (2).

For the considered therapeutic or preventive uses, molecules of general formula I may be administrated as such or in the form of suitable pharmaceutical composition, using conventional techniques and excipients. Typical pharmaceutical forms include aqueous, oleaginous suspension, dispersions as well as sterile powders, which may be used for the extemporaneous preparation of injectable solutions or dispersions. The compositions may also be solutions or suspensions in non-toxic diluents or solvents.

In the present invention it has been found that dimers and trimers of 3-hydroxybutyrate are much more effective than the monomer as antioxidants. In this respect reference is made to FIG. 1. However, if such dimers or trimers or other oligomers are intaken orally, they will decompose to monomers in the gastrointestinal tract, most likely due to the low pH in the stomach.

According to this invention, such decomposition in the gastrointestinal tract is prevented. Therefore the oligomers will reach their therapeutic target site in vivo in an uncleaved, non-decomposed form. Therefore, no loss of activity of the administered compound will occur.

In one embodiment, the oligomers are administered in a gastroresistant way. This means that the compounds are administered parenterally, locally (e.g. topically) or, if orally, e.g. as entero-tablets or -capsules or other entero-formulations. In the entero-formulation, the compound passes the stomach uncleaved.

Parenteral administration causes a systemic effect and includes, for example, intravenous, intramuscular, intraperitoneal, transdermal, subcutaneous, sublingual, pulmonal, nasal, rectal, and intravesical administration.

Local administration includes delivery as topical formulations such as ointments or creams; ear drops, eye drops, intraocular injections, intratumoral injections, etc. Entero-formulations have typically a shell or coating, which prevents decomposition already in the stomach.

In one embodiment, the present oligomers are administered in the form of intraocular injections. This is particularly useful for treatment of ocular degeneration, for example blue light induced ocular degeneration.

Another exemplary administration route is topical administration, e.g. by the use of dispersions, suspensions or solutions. Examples of these include ophthalmic drops, for example for treatment of ocular degeneration, The required amount of the active compound may depend on the particular condition to be treated. Any kind of pharmaceutically acceptable solid or liquid carrier or excipient known to those skilled in the medicinal and pharmaceutical arts, may be used in the pharmaceutical preparation.

Thus, generally speaking, the active component is used in effective amounts. The route of administration, already discussed above, the dosage as well as the exact formulation are chosen depending on the subject's condition. Thus, the interval can be adjusted individually to provide levels of the active compound in the blood plasma that are sufficient to maintain and obtain the desired therapeutic effects. In general, however, doses employed for humans typically are in the range of 0.0001 mg/kg to about 1000 mg/kg per day, in a range of about 0.01 mg/kg to about 500 mg/kg per dose of inhibitor.

Typically, the present oligomer, or mixture of oligomers, is administered at 0.01 to 100 mg/kg body weight, for example at 0.1 to 50 mg/kg body weight.

In practice, the dosage forms may comprise the active component in concentrations of about 0.1 to 250 mM, in particular about 0.5 to 100 mM, for example about 1 to 50 mM.

Amounts and regimens for the administration of the pharmaceutical compositions can be determined readily by those with ordinary skill in the clinical art of treating symptoms and disorders. Generally, the dosage depends on considerations such as age, gender and general health of the patient to be treated; kind of concurrent treatment, if any; frequency of the treatment and nature of the effect desired; duration of the symptoms; and other variables. A desired dose may be administered in one or more applications to obtain the desired results.

If desired, the pharmaceutical compositions according to the present embodiments may be provided as unit dosage forms.

The present oligomer(s) can be used as the single active pharmaceutical ingredient of the pharmaceutical composition or the oligomer(s) can be used together with other active components. Thus, for treatment of ophthalmic conditions, the present oligomer(s) can be combined with hyaluronic acid for example in ophthalmic drops or with ranibizumab in injectable compositions.

Means and methods for formulating the present pharmaceutical preparations are known to persons skilled in the art, and may be manufactured in a manner which is in itself known, for example, by means of conventional mixing, granulating, and dissolving, lyophilizing or similar processes.

As conventional, the pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition.

According to one embodiment the present invention concerns a pharmaceutical composition, including molecule of general formula I and one or more excipients.

Exemplary excipients are antiadherents (e.g. magnesium stearate), binders (e.g. saccharides such as sucrose, lactose, starches, cellulose, xylitol, sorbitol and maltitol, proteins such as gelatine, synthetic polymers such as polyvinylpyrrolidone and polyethylene glycol), coatings (e.g. hydroxypropyl methylcellulose), disintegrants (e.g. crosslinked polyvinylpyrrolidone, crosslinked sodium carboxymethyl cellulose and sodium starch glycolate), fillers (e.g. plant cellulose, mannitol, sorbitol, calcium carbonate, and magnesium stearate), flavours (e.g. mint, cherry, anise, peach, apricot, liquorice and vanilla), colours, lubricants (e.g. talk, silica, stearin, magnesium stearate and stearic acid), glidants, sorbents, preservatives (e.g. antioxidants, cysteine, methionine, citric acid, sodium citrate, parabens), and sweeteners (e.g. syrups and sugars).

Based on the above, in one embodiment, an injectable aqueous composition of the present oligomer(s) comprises oligomer(s), typically at 0.1 to 100 mg, together with one or more of α,α-trehalose optionally in the form of a salt, such as monohydrate or dihydrate, surfactants, such as polysorbate, histidine optionally in the form of a salt, such as hydrochloride or monohydrate.

In the food additive, any non-toxic carrier or excipient acceptable for use in food can be mixed with a present molecule of general formula I composition. The food product according to this invention is especially a functional food, a nutritional supplement, a nutrient, a pharmafood, a nutraceutical, a health food, a designer food or any food product. The functional food according to this invention can, for example be in form of biscuits, bread, cake, candy, dairy product or cereal. Exemplary dairy products are milk, butter, vegetable oil, mixture of butter and vegetable oil, yoghurt, cheese, and ice cream.

According to one embodiment the present invention concerns use of molecules of general formula I

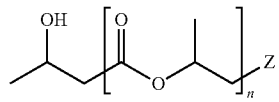

wherein n is an integer 1 or 2, and wherein Z is selected from carboxylic acid (Z=COOH) and its salt and an ester (COOR) as an antioxidant. Exemplary esters are alkyl and aryl esters. Alkyl esters are preferable. Exemplary alkyl groups are methyl, ethyl, n-propyl, i-propyl, n-butyl, sec-butyl and tert-butyl. A particular alkyl group is methyl. The alkyl group may include also heteroatoms, such as one or more of the following: halogen, oxygen, sulfur. Exemplary salts when Z=COOH are sodium, potassium, lithium, magnesium, calcium and ammonium salts.

According to a particular embodiment the present invention concerns the use of molecules of general formula I, wherein n is 1 or 2, and wherein Z is COOMe as antioxidant. These molecules have the following structures:

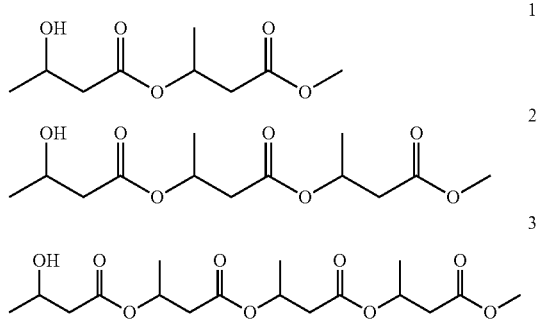

Particularly preferable molecules for use as a medicament are the dimer (1) and the trimer (2). These molecules of general formula I are water soluble and they can enter cells by simple diffusion or they can be carried by transporters.

Figure 2:
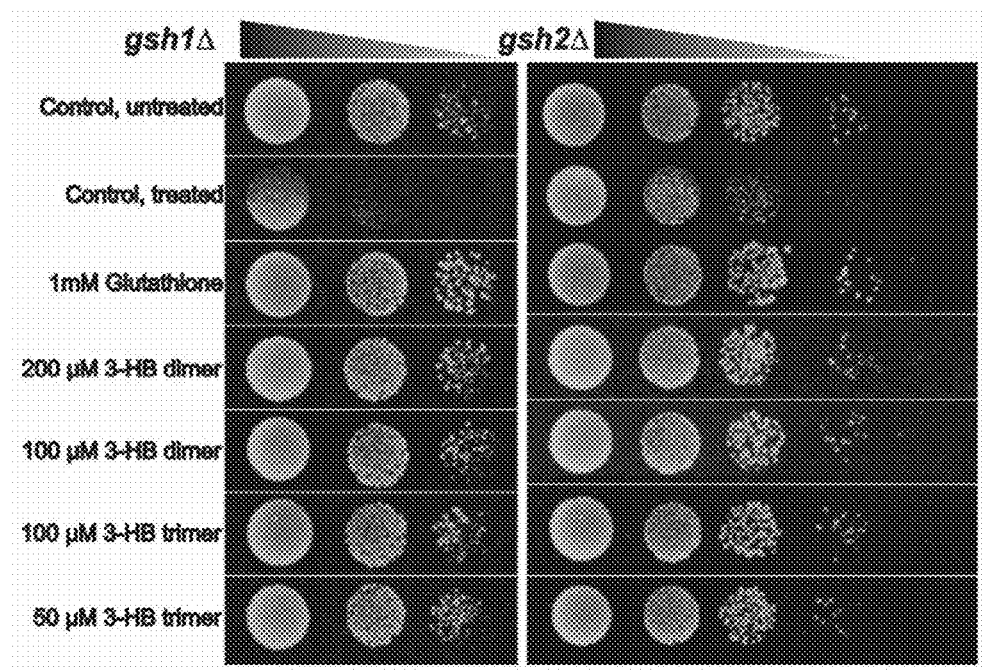
FIG. 2 shows reversal of hypersensitivity of yeast GSH pathway deletion mutants gsh1Δ and gsh2Δ to hydroxyl radical stress (2.5 mM $H_2O_2$, 65 μM $FeCl_3$) by treatment from top to bottom: untreated control (no stress, no antioxidants); treated control (stress, no antioxidants), glutathione, 3-HB dimer (compound 1), and 3-HB trimer (compound 2)

Exemplary uses of compounds of general formula I as antioxidants are disclosed in FIGS. 1 and 2.

As shown in FIG. 1, the dimer (1; FAA-1) and the trimer (2; FAA-2) have significantly better hydroxyl radical scavenging activity than the prior art antioxidants L-ascorbic acid, L-glutathione and 3-hydroxybutyric acid. As shown in FIG. 2, the antioxidants of the present invention show increase of survival from the hydroxyl radical stress of eukaryotic yeast cells 10 to 100 fold compared to glutathione.

According to one embodiment the present invention concerns use of a molecule of general formula I

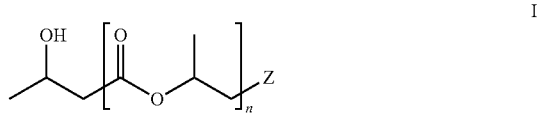

wherein n is an integer 1 or 2, and wherein Z is selected from carboxylic acid or its salt or an ester as a protecting agent against oxidative stress of cells.

The preferred molecules are the following:

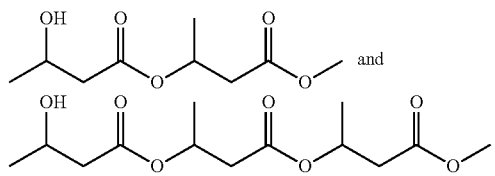

It is known that several plant tissues such as pluripotent callus tissues of Scots pine are difficult to grow as the oxidative stress affects the growth and viability, which can be seen as rapid browning. In the present invention it was found that the proliferation and viability of cells, such as animal and plant cells, can be increased by culturing the cells in the presence of the antioxidants selected from molecules of general formula I, wherein n is from 1 to 5, preferably molecules of formulas 1 or 2.

Thus in one embodiment, 70-78% of bud tissues grown in the presence of 1 and 2 showed persistent viability, compared to only 30-54% of control bud samples, over a three-week period.

Figure 3:
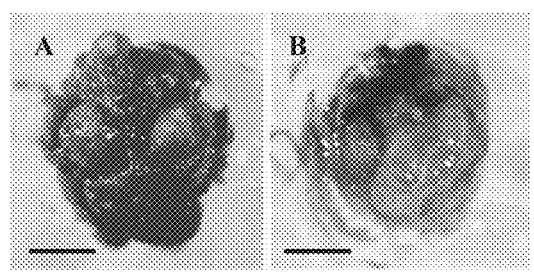
FIG. 3 show shoot tip of Scots pine grown on A) control medium and B) medium including molecules of formula (1) and (2) after 5 weeks. Scale bar=1 mm.

FIG. 3 shows the situation where a shoot tip of Scots pine is grown in a medium in the A) absence, and B) presence, of molecules (1) and (2). The shoot tip grown in the absence of the antioxidants of the present invention is dead, while the shoot tip grown in the presence the antioxidants of the present invention is alive after five weeks.

According to an embodiment the present invention concerns a method for increasing proliferation and viability of cells, in particular plant cells, the method comprising growing the cells in the presence of molecule of general formula I,

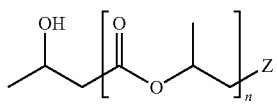

wherein n is an integer 1 or 2, and wherein Z is selected from carboxylic acid or its salt and ester. Particular molecules used for the method are the following:

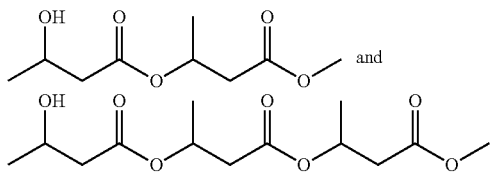

Based on the above-discussed valuable properties of the present oligomers they can also be employed in growth media for microorganisms, such as in growth media for yeasts and bacteria, both in cell culture and microbiological culture media. Examples include nutrient broths.

Typically, the concentration of the oligomers in growth media is about 0.1 to 250 mM, in particular about 0.5 to 100 mM, for example about 1 to 50 mM.

Molecules of general formula I as well as Formulas 1 to 3 can be obtained from polyhydroxybutyrate, which is a commercially available product, by hydrolyzation and by isolation, for example by extraction, and purification by chromatography.

Thus, in one embodiment, as will be exemplified below, molecules of general formula I and, in particular of formulas 1 and 2, can be prepared from the corresponding polymer by degradation in a method comprising the steps of:
dissolving poly 3-hydroxybutyric acid in a solvent preferably under heating and stirring to form a solution;
adding an acid to the solution to form an acidified solution;
heating the acidified solution under refluxing conditions to hydrolyze the poly 3-hydroxybutyric acid to oligomers;
optionally esterifying the oligomeric acids; and
recovering the oligomers optionally in the form of esters.

In the acidification step, preferably organic acids are employed, such as p-toluene sulphonic acid, but also mineral acids can be used, such as hydrochloric acid.

The solvent is preferably an aprotic compound, such as a chlorinated aliphatic solvent, for example dichloromethane or dichloroethane. Other aprotic compounds that can be used are nitromethane and acetonitrile.

Esterification involves the step of contacting the oligomeric acids, or reactive derivatives thereof, with an esterification agent. Esterification can also be carried out simultaneously with the hydrolysis for example by adding an esterification agent, such as an alcohol, to the hydrolysis solution. Esterification is optionally carried out in the present of a catalyst, such as an acid or alkaline catalyst, preferably an acid catalyst. For example, p-toluene sulphonic acid works both as an acid agent for achieving hydrolysis and as an acid catalyst for esterification.

The recovering step can comprise any conventional technique for separating solutes from solutions, including e.g. solvent extraction, in particular liquid-liquid extraction. In this extraction step, typically a polar or ionic solvent can be used. Examples include ammonium acetate.

Further, in the recovering step the oligomers can be further separated from each other and various oligomers purified by chromatography, such as isocratic flash chromatography.

The oligomers can also be isolated from bacteria, as discussed below.

The following non-limiting examples illustrate embodiments of the present technology:

EXPERIMENTAL

Preparation of Compounds 1 and 2

Molecules of structure 1 and 2 were prepared from 3-HB polymer by degradation. Accordingly, Poly 3-hydroxybutyric acid (PHB) was depolymerized as disclosed by Athlan et al. (1997) with minor modifications. A half gram of PHB was dissolved in 35 ml of dichloroethane by heat and stirring. Before refluxing, 75 mg of p-toluenesulfonic acid and 25 ml of methanol was added. The method was optimized to a reflux time of 16 h for the maximum yield. A liquid-liquid extraction was made twice using 5 mM ammonium acetate, and the aqueous phases were collected and freeze-dried.

The oligomers were diluted to eluent (40% MeOH) and purified with isocratic flash chromatography (Sepra C-18-E, 50 μm (Phenomenex) sorbent). From the 10 ml/min flow, 1-minute fractions were collected. The fractions containing compounds 1 and 2 were purified further with preparative-scale HPLC equipped with 1525 binary pump, 2998 photodiode array detector, UV fraction manager, 2767 sample manager, and Atlantis prep T3 OBD 5 μm column (19×50 mm). The injection volume was 500 μl and the HPLC gradient consisted of 0.1% $CH_3CO_2H$ (A) and methanol (B). The gradient was started from 20% of B, changing linearly to 100% B in 10 min, and 48-s fractions were automatically collected at the flow rate of 20 ml/min. Compounds 1 and 2 were identified by TOF-MS and NMR analysis.

Separation of Molecules of Formulas 1 and 2 from *Methylobacterium extorquens* DSM13060

*M. extorquens* DSM13060 (Wild type; a plant growth-promoting conifer endophyte; Pirttilä et al 2000) was grown to stationary phase (4 days) at room temperature in DM1 medium (D1 medium without growth regulators; Hohtola 1988, Pirttilä et al. 2008), and bacterial cells were removed by centrifugation and filtering through 0.2 mm filters (Schleicher & Schuell, Keene, N.H.) to obtain sterile conditioned medium. The conditioned medium was freeze-dried and fractioned by gradient flash chromatography (Sepra C-18-E, 50 μm [Phenomenex] sorbent) with 0.1% formic acid and acetonitrile. The compounds present in each fraction were analyzed by LC-MS. The conditioned DM1 medium was fractionated into 10 parts by semi-preparative HPLC, each containing at most one 3-HB oligomer.

Yeast Strains, Growth Media and Culture Conditions

Yeast strains (gsh1Δ (YJL101c) and gsh2Δ (YOL049w); EUROSCARF) were streaked from glycerol stocks onto YEPD agar plates (1% w/v Bacto yeast extract; 2% w/v Bacto peptone; 2% w/v D-glucose; 2% w/v agar) and incubated at +30° C. for 48 h. Yeast pre-cultures were inoculated from the plates and grown in liquid SG minimal medium (0.67% w/v yeast nitrogen base without amino acids; 2% w/v glucose with appropriate supplements: uracil, 0.02 mg/ml; amino acids, 0.03 mg/ml) at +30° C. in orbital shaker with 180 rpm to stationary phase (1.0-1.2 $OD_{600}$). Growth was measured spectrophotometrically at 600 nm ($OD_{600}$) and the cell densities were adjusted to 1.0 OD600 before inoculation of the final density of 0.25 $OD_{600}$ into each assay reaction.

HOSC Assay (Fluorometric .OH Scavenging Capacity Assay)

Assay reactions were prepared according to Moore et al. (2006) and analyzed in black 96-well polystyrene plates (FluoroNunc, Thermo Scientific) with a Victor3 multilabel plate reader (PerkinElmer, Turku, Finland). Each reaction mixture contained 170 μl of $9.28 \times 10^{-8}$ M fluorescein (FL) prepared in 75 mM sodium phosphate buffer (pH 7.4), 30 μl of blank or sample or standard, 40 μl of 0.1990 M $H_2O_2$, and 60 μl of 3.43 mM $FeCl_3$, pipetted to the 96-well plate in same order. Trolox standards (20, 40, 60, 80, and 100 μM), control solutions of glutathione, vitamin C, 3-HB monomer (3-hydroxybutyric acid, 3-HBA) (Sigma-Aldrich, St. Louis, Mo.), and the 3-HB oligomer samples were freshly prepared in 50% acetone for each assay. Each reaction was pipetted onto the 96-well plate in triplicate. Fluorescence was measured at the excitation wavelength of 485 nm and the emission wavelength of 535 nm. Read time for each well was 0.1 s, and each plate was read once per minute for 3 h. Based on the area under the curve (AUC) of the Trolox concentrations and the net area under the fluorescein decay curve (Ou et al. 2001), the relative HOSC values were calculated by using the regression equation for the pure compounds. Values were expressed as Trolox equivalents (TE), where one micromole of TE corresponds to one micromole of sample. The experiment was repeated three times.

Calculation of Area Under Curve (AUC) Values:

$$AUC = 0.5 + f1/f0 + f2/f0 + f3/f0 + \ldots + fi-1/f0 + 0.5(fi/f0)$$

f0=the initial fluorescence reading at 0 min
fi=the final fluorescence reading

Calculation of Relative HOSC Values for Pure Compounds:

$$[(AUC_{sample} - AUC_{blank})/(AUC_{Trolox} - AUC_{blank})] \times (\text{Molarity of Trolox/Molarity of sample})]$$

Iron-Catalyzed Hydroxyl Radical Formation by Haber-Weiss Driven Fenton Reaction (Liochev 1999, Kehrer 2000):

  (1)

  (2)

The Net Reaction:

  (3)

Fluorometric .OH scavenging capacity (HOSC) assays for 3-HB mono-, di- and trimers (molecules of general formula 1, wherein n is 1 and 2, respectively), along with glutathione and ascorbic acid was performed. The radical scavenging capacity of these compounds was compared under Fenton's reaction, against Trolox, an analog of vitamin E. As shown in FIG. 1, both 3-HB di- and trimers were 3-times better .OH scavengers than glutathione, a thiol responsible for intracellular redox homeostasis in living cells, and 10-times better than ascorbic acid, the most common antioxidant found in nature. 3-HB di- and trimers showed also 10-times better scavenging capacity when compared to the commercial 3-HB monomer, 3-hydroxybutyric acid (3-HBA). Oligomers of 3-HB having a chain length longer than four units had low antioxidant activity.

The 3-HB monomer, 3-hydroxybutyric acid, is ubiquitous, found in all living organisms. In mammals, it was recently reported to have ROS scavenging capacity, preventing lipoperoxidation and neuronal death (Haces et al. 2008), and inhibiting histone deacetylases during oxidative stress (Shimazu et al. 2013). In the present invention it has been shown that methyl-esterified 3-HB di- and trimers, have more than 10-fold hydroxyl radical scavenging-capacity compared to the monomer 3-hydroxybutyric acid.

Hydroxyl Radical-Induced Growth Arrest Bioassay for Yeast

To validate the alleviation of oxidative stress in living cells and to identify the cellular target proteins for hydroxyl radical scavenging in eukaryotic cells, a yeast deletion mutant bioassay was developed on the basis of HOSC assay (Moore et al. 2006). Hydroxyl radicals were generated under physiological pH (7.4) in Fenton-like $Fe^{3+}/H_2O_2$ reaction. The original assay settings were adjusted for yeast cells in phosphate buffered SG medium, and the pH and $O_2$ levels were monitored by SENBIT® system (Vasala et al. 2006). The concentration of hydrogen peroxide was optimized to a sub-lethal level (2.5 mM) and the reaction was supplemented with appropriate amount of $FeCl_3$ (0.0646 mM) to produce a constant flux of .OH radicals.

The total reaction volume was down-scaled to 1 ml, which made the assay suitable for the natural products low in quantity. The assay reactions were pipetted to sterile 15-ml snap-cap tubes in the following order: 612 μl of 74 mM sodium phosphate buffer (pH 7.4), 25 μl of 100 mM $H_2O_2$, 12.9 μl of 5 mM $FeCl_3$, the test compound or the control, and water up to the total volume of 100 μl. Based on the previous HOSC assay results, 1 mM glutathione (reduced) was used as the positive antioxidant control.

The monomer of 3-hydroxybutyric acid (3-HBA) (Sigma-Aldrich, St. Louis, Mo.) was tested in concentrations of 20 mM, 10 mM, 5 mM and 2.5 mM for screening of yeast strains sensitive to .OH.

The dimer of 3-hydroxybutyrate (1) was tested in 200 μM and 100 and the trimer (2) was tested in concentrations of 100 μM and 50 μM. Finally, 250 μl of yeast culture was diluted to 1.0 OD600 in SG medium and added to the reaction to make the final cell density of 0.25 OD600.

The assay reactions were incubated at +30° C. in an orbital shaker with 195 rpm for 6 hours in a tilted position to ensure aeration. Five 10-fold serial dilutions resulting in six individual samples from $1 \times 10^6$ (100) to 100 ($1 \times 10^{-5}$) cells were prepared in a sterile 96-well plate and spotted with a multi-channel pipette onto SG agar plates, resulting in six individual 4-μl spots per treatment.

Up to five separate treatments were pipetted per Petri plate including the treated control ($H_2O_2 + FeCl_3$, without antioxidant), untreated control ($H_2O$, no oxidative stress), positive control (H₂O₂+FeCl₃, 1 mM glutathione), and the test compounds. All treatments were pipetted in triplicate, and the experiment was repeated three times. Cell growth was monitored at +30° C. for 72 hours and Petri plates were scanned digitally to high-quality computer images after 48 and 72 hours. Hydroxyl radical-induced stress and the alleviation of stress by antioxidant compounds in various deletion mutant strains of *S. cerevisiae* were evaluated visually.

Viability Assay on Pine Shoot Tips

Shoot tips (n=9-13) of Scots pine (*Pinus sylvestris* L.) were collected from young (>10 years) trees and surface-sterilized in 70% ethanol for 1 min and in 6% Ca(ClO)₂ for 20 min, and rinsed thoroughly three times with sterile water. After rinsing in sterile water, the shoot tips (buds) were aseptically peeled in a laminar flow hood and placed on the media. The pine shoot tips were grown in 8/16 h photoperiod at +25±1° C. in the presence and absence of molecules of general formula I, wherein n is from 2 to 10. The viability of the pine tissue was assessed for up to 6 weeks visually (FIG. 3) and by 1% (w/v) acetocarmine staining. The viability on each fraction was recorded as percentage of live buds. The experiment was twice with each oligomer (mono- to decamer) on each Petri plate containing 18-31 pine shoot tips.

Further embodiments of the present invention are disclosed in the following numbered clauses.

1. A method of preventing and/or inhibiting development of a disorder or condition related to oxidative stress in a human or animal subject in need thereof by administering an efficient amount a composition comprising a molecule of general formula I,

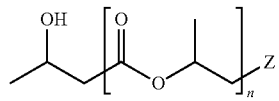

wherein n is from 1 to 10, in particular from 1 to 5, for example 1 to 4, advantageously 1 to 3, preferably 1 or 2, and wherein Z is selected from an ester, carboxylic acid or its pharmaceutically acceptable salt, to said subject.

2. The method according to clause 1 wherein said disorder is a neurodegenerative disorder.

3. The method according to clause 2, wherein the neurodegenerative disorder is selected from a group consisting of Huntington's disease, Parkinson's disease, Alzheimer's disease, Lou Gehrig's disease, multiple sclerosis.

4. The method according to clause 2 wherein the neurodegenerative disorder is a retinal neurodegenerative disorder.

5. The method according to clause 4, wherein the retinal neurodegenerative disorder is selected from retinitis pigmentosa, age-related macular degeneration, glaucoma, diabetic retinopathy.

6. The method according to clause 1, wherein the composition comprises the molecule according to general formula I, wherein n is an integer from 1 to 4, advantageously 1 to 3, preferably 1 or 2, and one or more excipients.

7. The method according to clause 1, wherein the molecule of general formula I is selected from

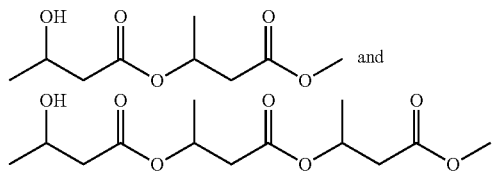

8. The method according to any of clauses 1 to 7, wherein the molecule of general formula I is administered in a gastroresistent way, for example parenterally, locally, such as topically, or, if orally, e.g. as entero-tablets or -capsules or other entero-formulations, in particular to allow for the compounds to pass the stomach in uncleaved or non-decomposed form.

9. A molecule of general formula I,

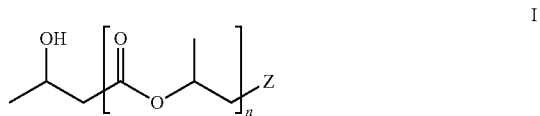

wherein n is from 1 to 10, in particular from 1 to 5, for example 1 to 4, advantageously 1 to 3, preferably 1 or 2, and wherein Z is an ester, in particular an ester of having the formula COOR, wherein R stands for an alkyl group, in particular a lower alkyl group, selected from the group of methyl, ethyl, n-propyl, i-propyl, n-butyl, sec-butyl and tert-butyl, said alkyl group optionally including heteroatoms, such as one or more of the group of halogen, oxygen and sulfur.

The specific examples provided in the description given above should not be construed as limiting the scope and/or the applicability of the appended claims.

INDUSTRIAL APPLICABILITY

The present invention provides for the pharmaceutical use of molecules of General formula I for example for treating, preventing and/or inhibiting development of a disease, disorder or condition related to oxidative stress.

Exemplary diseases are neurodegenerative disorders, in particular the present compounds are used for treating, preventing or inhibiting development of ophthalmic degeneration, such as ocular or retinar degeneration The use of the present oligomers for increasing proliferation and viability of cells, in particular plant cells, as well as in growth media for microorganisms, is also foreseen.

LIST OF REFERENCES

Patent Literature

WO2008110034
US 20020013339
WO 2006020179
US 2009253781
WO 0004895
JP 2005065652
WO 2009089144

Non-Patent Literature

Athlan, A, Braud, C., Vert, M, (1997) Abiotic aging of water-soluble 3-hydroxybutyric acid oligomers as monitored by capillary zone electrophoresis. *J. Environ. Polymer Degradation.* 5, 243-247.

Berge S M, Bighley L D, Monkhouse D C (1977) Pharmaceutical salts. *J. Pharm Sci,* 66: 1-19.

Haces M L, Hernandez-Fonseca K, Medina-Campos O N, Montiel T, Pedraza-Chaverri J, Massieu L (2008) Antioxidant capacity contributes to protection of ketone bodies against oxidative damage induced during hypoglycemic conditions. *Exp. Neurol.* 211: 85-96.

Hohtola, A., (1988) Seasonal changes in explant viability and contamination of tissue cultures from mature Scots pine. *Plant Cell, Tissue and Organ Culture.* 15, 211-222.

Liochev, S. I. (1999). The mechanism of "Fenton-like" reactions and their importance for biological systems. A biologist's view. Metal ions in biological systems, 36, 1.

Kehrer, J. P. (2000). The Haber-Weiss reaction and mechanisms of toxicity. Toxicology, 149(1), 43-50.

Moore J, Yin J J, Yu L L (2006) Novel fluorometric assay for hydroxyl radical scavenging capacity (HOSC) estimation. *J. Agric. Food Chem.* 54: 617-26.

Ou B, Hampsch-Woodill M, Prior R L (2001) Development and validation of an improved oxygen radical absorbance capacity assay using fluorescein as the fluorescent probe. *J. Agric. Food Chem.* 49, 4619-4626.

Pirttilä A M, Laukkanen H, Pospiech H, Myllyla R, Hohtola A (2000) Detection of intracellular bacteria in the buds of Scots pine (*Pinus sylvestris* L.) by in situ hybridization. *Appl. Env. Microbiol.* 66:3073-3077.

Pirttilä A M, Podolich O, Koskimaki J J, Hohtola E, Hohtola E (2008) Role of origin and endophyte infection in browning of bud-derived tissue cultures of Scots pine (*Pinus sylvestris* L.). Plant Cell, Tissue and Organ Culture. 95, 47-55.

Shimazu T, Hirschey M D, Newman J, He W, Shirakawa K, Le Moan N, Grueter C A, Lim H, Saunders L R, Stevens R D, Newgard C B, Farese Jr. RV, de Cabo R, Ulrich S, Akassoglou K, Verdin E (2013) Suppression of oxidative stress by β-hydroxybutyrate, an endogenous histone deacetylase inhibitor. *Science* 339: 211-214.

Vasala A, Panula J, Bollok M, Illman L, Halsig C, Neubauer P. (2006) A new wireless system for decentralised measurement of physiological parameters from shake flasks. *Microb. Cell. Fact.* 5, 8.

The invention claimed is:

1. A method of treatment of an individual having an ophthalmic disorder, said method comprising:

administering to the individual a therapeutically effective amount of a molecule of general formula I, $$\text{OH} \quad \left[ \begin{array}{c} \text{O} \\ \end{array} \right]_n \text{Z} \qquad \text{I}$$

wherein
n is an integer 1 or 2, and
Z is selected from a carboxylic acid, its pharmaceutically acceptable salt or ester and the disorder is associated with oxidative stress.

2. The method according to claim 1, wherein said method is for the treatment of an individual having a retinal neurodegenerative disorder.

3. The method according to claim 2, wherein said retinal neurodegenerative disorder is selected from the group of retinitis pigmentosa, age-related macular degeneration, glaucoma and diabetic retinopathy.

4. The method according to claim 1, wherein said molecule is administered in a topical formulation selected from the group consisting of: an ointment, cream, ear drops, eye drops, intraocular injection and intratumoral injection.

5. The method according to claim 4, wherein said topical formulation is an intraocular injection or ophthalmic drops.

6. The method according to claim 1, wherein Z is an ester.

7. The method according to claim 1, wherein n is an integer 1 or 2, and wherein preferably Z is an ester having the formula COOR, wherein R stands for a lower alkyl group with 1 to 4 carbon atoms.

8. The method according to claim 1, wherein the molecule of general formula I is selected from 9. The method according to claim 1, wherein Z has the formula COOR and wherein R stands for an alkyl group, said alkyl group being selected from the group of methyl, ethyl, n-propyl, i-propyl, n-butyl, sec-butyl and tert-butyl, said alkyl group optionally including heteroatoms, such as one or more of the group of halogen, oxygen and sulfur.

10. The method according to claim 9, wherein R is a lower alkyl group.

11. The method according to claim 9, wherein R is a lower alkyl group having 1 to 6 carbon atoms.

12. The method according to claim 9, wherein R is a lower alkyl group having 1 to 4 carbon atoms.

* * * * *